United States Patent [19]

Nichols, Jr.

[11] 4,173,094

[45] Nov. 6, 1979

[54] METHOD FOR TREATING GROUND SURFACES WITH A TOXIC AGENT

[76] Inventor: Wallace H. Nichols, Jr., 4752 Lark Ridge Cir., Sarasota, Fla. 33581

[21] Appl. No.: 852,315

[22] Filed: Nov. 17, 1977

[51] Int. Cl.$^2$ ............................................. A01M 17/00
[52] U.S. Cl. ......................................... 43/129; 44/79; 239/129
[58] Field of Search ................. 43/124, 127, 129, 132, 43/138; 239/129; 44/79; 111/7

[56] References Cited

U.S. PATENT DOCUMENTS

| | | | |
|---|---|---|---|
| 1,717,911 | 6/1929 | Brewer | 111/7 |
| 2,402,402 | 6/1946 | Hickman | 43/129 |
| 2,759,292 | 7/1956 | Whipple | 43/129 |
| 2,865,671 | 12/1958 | Jensen | 43/129 |
| 3,205,176 | 9/1965 | Tenney | 43/129 |
| 3,244,641 | 6/1966 | Durr | 43/129 X |
| 3,309,268 | 3/1967 | Sherman | 44/79 |

*Primary Examiner*—Nicholas P. Godici

[57] ABSTRACT

A composition for dispensing toxic agents, such as an insecticide, comprises an internal combustion engine fuel containing a minor amount of an insecticide which is refractory to the fuel combustion conditions of the engine and soluble in the fuel. The proportion of insecticide in the mixture is low enough to enable operation of the engine to power a vehicle such as a lawn mower and high enough to be effective in the engine exhaust against target pests. In use, a gasoline fuel containing up to 10% by weight of malathion is employed to operate an internal combustion engine powering an implement such as a lawn mower and the insecticide is dispensed via the engine exhaust over the ground traversed by the implement.

5 Claims, No Drawings

METHOD FOR TREATING GROUND SURFACES WITH A TOXIC AGENT

BACKGROUND OF THE INVENTION

The present invention concerns a composition for dispensing a toxic agent through the exhaust of an internal combustion engine, and a method for dispensing such a toxic agent. More particularly, the invention is concerned with a fuel composition containing a minor but effective amount of an insecticide or other toxic agent such as a fungicide or herbicide.

It is known to attempt to introduce an ingredient such as an insecticide into the exhaust pipe of an internal combustion engine operating a lawn mower or the like. It is also known to provide apparatus to create a fog or smog by combusting part of a mixture to provide heat to vaporize and dispense the balance of the mixture. The former concept is illustrated in U.S. Pat. Nos. 2,759,292 (Whipple et al); 2,865,671 (Jensen) and 3,205,176 (Tenney). Each of these patents provides apparatus for injecting an agent to be dispensed into the exhaust of an engine and provides means to overcome problems such as engine back pressure, control of feeding rate, etc.

The second mentioned concept, that of providing a fog, is illustrated in U.S. Pat. No. 2,402,402 (Hickman). Hickman discloses a composition including a minor amount of gasoline with a major amount of fuel oil and an insecticide, rotenone. The mixture is passed through the Hickman apparatus in which a vapor portion of it is combusted to vaporize the balance.

These prior art attempts involve the provision of separate apparatus to dispense the agent. Hickman is illustrative of a special apparatus required solely to carry out the creation and dispensing of a fog. The other patents are illustrative of the concept of providing auxiliary apparatus to inject an agent downstream of the combustion chamber of an engine for dispersal thereof by the engine exhaust.

It is an object of the present invention to provide a novel composition dispensable by an internal combustion engine of conventional design without necessity for any auxiliary equipment attached to the engine.

It is another object of the present invention to provide a novel method for dispensing a toxic agent by incorporating the agent into the fuel of an internal combustion engine and dispensing the agent as a part of the engine exhaust, the agent having passed through the combustion engine with the fuel.

SUMMARY OF THE INVENTION

In accordance with the present invention, there is provided a composition for dispensing a toxic agent through the exhaust of an internal combustion engine, the composition comprising a mixture of a minor amount of one or more organic toxic agents effective to control target pests with a major amount of internal combustion engine fuel. The proportion of fuel in the mixture is sufficient to enable operation of an internal combustion engine fueled thereby. The toxic agents are selected from the class consisting of insecticides, fumigants and herbicides which are soluble in the fuel and refractory to fuel combustion conditions of the fueled engine. The toxic agents are present in the mixture in an amount at least sufficient to provide, in the exhaust of the fueled engine, an amount of the toxic agent which is effective against such target pests.

Certain objects of the invention are attained when the fuel is gasoline and the toxic agent is an insecticide comprising either a halogenated hydrocarbon or an organophosphorous compound. The insecticide may be selected from aldrin, chlordane, dieldrin, DDT, heptachlor, malathion and mirex and be present in the amount of between about 2½% to 10% by weight of the mixture. Other objects of the invention are attained by a composition for dispensing an insecticide through the exhaust of an internal combustion engine, the composition comprising a mixture of a minor amount of one or more insecticides effective to control target insects, with a major amount of internal combustion engine fuel, the proportion of fuel in the mixture being sufficient to enable operation of an internal combustion engine fueled thereby. The insecticides are soluble in the fuel, refractory to fuel combustion conditions in the fueled engine and present in the mixture in an amount at least sufficient to provide, in the exhaust of the fueled engine, an amount of said insecticide which is effective against such target insects.

Certain objects of the invention are attained when the insecticide is malathion and is present in the amount of between about 2½% to 10% by weight of the mixture. The fuel may be a kerosene-gasoline mixture.

The invention also provides a method of dispensing a toxic agent over a ground area comprising supplying to an internal combustion engine operating a ground vehicle a fuel comprising a mixture of a minor amount of one or more organic toxic agents effective to control target pests with a major amount of internal combustion engine fuel. The proportion of fuel in the mixture is sufficient to enable operation of an internal combustion engine fueled thereby. The toxic agents are selected from the class consisting of insecticides, fumigants and herbicides which are soluble in the fuel and refractory to fuel combustion conditions of the fueled engine and the toxic agents are present in said mixture in an amount at least sufficient to provide in the exhaust of the fueled engine, an amount of the toxic agent which is effective against such target pests. The method includes a step of discharging engine exhaust from the fueled engine as it moves over the ground area into the atmosphere with the toxic agent depositing upon ground and foliage surfaces.

The step of supplying the mixture may comprise the step of supplying a mixture of a minor amount of an insecticide with a major amount of gasoline.

DESCRIPTION OF THE PREFERRED EMBODIMENTS

A fuel mixture for use in an internal combustion engine, in accordance with the invention, must enable operation of the engine notwithstanding the presence of a toxic agent in an amount sufficient to provide in the engine exhaust a concentration of the toxic agent which is effective against target pests.

Since the invention contemplates using a fuel composition containing a organic toxic agent, or otherwise introducing a toxic agent into the combustion chamber, i.e., the cylinders of an internal combustion engine, the toxic agent must be sufficiently refractory to survive passage through the firing chamber without being destroyed or rendered into an innocuous composition or one which is ineffective against the target pests.

Further, the toxic agent must be soluble in the fuel so as to pass through the engine, carburetor or other components without causing problems of blockage.

Generally, halogenated hydrocarbon compounds and organophosphorous compounds employed as insecticides meet the foregoing requirements when present in suitable amount in a hydrocarbon fuel for internal combustion engines.

As used herein and in the claims, the term "soluble" is intended to include liquid toxic agents which are miscible with a liquid hydrocarbon fuel, solids which are soluble in the fuel and solutions of solids or liquids in a carrier vehicle, which solutions are soluble in the fuel. Thus, for example, a liquid insecticide or a solution of an insecticide in a carrier liquid which is miscible with a gasoline fuel is deemed to be soluble in the fuel.

The fuel may be any convenient fuel for the internal combustion engine to be employed, such as a diesel fuel or gasoline. The gasoline may include other components such as the lubricating oils commonly mixed with gasoline intended for use in two-cycle gasoline engines.

"Gasoline" and "kerosene" as used herein have their usual and conventional meanings identifying hydrocarbon fuels employed as gasoline engine fuels, a lighting or heating fuel in gasoline or kerosene lanterns, stoves and the like. Gasoline is a relatively low boiling point fraction usually obtained, at least in part, by cracking of petroleum fractions. Kerosene is usually a somewhat higher boiling point fuel oil fraction of petroleum.

The toxic agent may be any suitable insecticide, fumigant or herbicide, including fungicides, etc.

Among the insecticides believed to be suitable for incorporation into a gasoline or gasoline-kerosene fuel mixture are the following halogenated hydrocarbon compounds: aldrin, chlordane, dieldrin, DDT, heptachlor, malathion and mirex.

Also suitable are organophosphorous compounds such as malathion. Other insecticides are also believed to be effective include halogenated hydrocarbons such as BHC, TDE, methoxychlor, toxaphene, CPCBS, CPBS, BPIPS, carbon tetrachloride, methyl bromide, ethylene dibromide, ethylene dichloride, tetrachloroethane and chloropicrin; and organophosphorous compounds such as TEPP, parthion, paraoxon, TPAM, schradan, dimefox, mipafox, systox and EPN.

The following table provides a chemical description of the foregoing identified insecticides:

Table I

| Common Name | Chemical Name |
| --- | --- |
| A. Halogenated Hydrocarbon Insecticides | |
| BHC, | 1, 2, 3, 4, 5, 6 hexachlorocyclohexan |
| gamma--BHC | (Benzene hexachloride), gamma-isomer thereof. |
| DDT | Mixture of isomers of dichloro-diphenyl-trichloro ethane, usually predominantly pp'-DDT (1,1,1-Trichloro-2,2-di-(p-chlorophenyl)-ethane) |
| TDE | 1,1-Bis (p-chlorophenyl)-2,2-dichloroethane |
| Mirex (Dechlorane) | Dodecachlorooctahydro-1, 3, 4, -metheno-1H-cyclobuta [cd]-pentalene. |
| Methoxychlor | 1, 1, 1-Trichloro-2, 2-di-(4-methoxyphenyl)-ethane |
| Dieldrin | Contains not less than 85% of 1, 2, 3, 4, 10, 10-hexachloro-6, 7-epoxy-1, 4, 4a, 5, 6, 7, 8, 8a-octahydro-1,4, 5, 8-dimethanonaphthalene, and not more than 15% of insecticidally active related compounds |
| Aldrin | Contains not less than 95% of 1, 2, 3, 4, 10, 10-hexachloro-1, 4, 4a, 5, 8, 8a-hexahydro-1, 4, 5, 8-dimethanonaphthalene, and not more than |

Table I-continued

| Common Name | Chemical Name |
| --- | --- |
| | 5% of insecticidally active related compounds |
| Toxaphene | Chlorinated camphene (67–69% chlorine) |
| Heptachlor (Drinox) | 74% 1, 4, 5, 6, 7, 8, 8a-heptachloro-3a, 4, 7a-tetrahydro-4, 7-methanoindene |
| Chlordane | 2, 3, 4, 5, 6, 7, 10, 10-Octachloro-4, 7, 8, 9-tetrahydro-4, 7-endomethyleneindan |
| CPCBS | 4-Chlorophenyl-4-chlorobenzene sulfonate |
| PCPBS | 4-Chlorophenylbenzene sulfonate |
| BPIPS | 2-(p-tert-Butylphenoxy)isopropyl 2-chloroethyl sulfite |
| Carbon tetrachloride | Carbon tetrachloride |
| Methyl bromide | Methyl bromide |
| Ethylene dibromide | Ethylene dibromide |
| Ethylene dichloride | Ethylene dichloride |
| Tetrachloroethane | Tetrachloroethane |
| DD | 1, 2-Dichloropropane, 1, 3-dichloropropylene in approximately equal proportions |
| Chloropicrin | Chloropicrin |
| B. Organophosphorus Insecticides | |
| TEPP (HETP) | Tetraethyl pyrophosphate |
| Parathion | 0,0 Diethyl o, p-nitrphenyl thion phosphate |
| Paraoxon | Diethyl-p-nitrophenyl phosphate |
| TPAM | Diethylthiophosphoric acid ester of 7-hydroxy-4-methylcoumarin |
| Malathion | 0,0 Dimethyl dithiophosphate of diethyl mercaptosuccinate [formerly known as S-(1, 2-dicarboxyethyl)-0,0-dimethyl dithiophosphate] |
| Schradan | Bisdimethyl-aminophosphonous anhydride or octamethylpyrophosphoramide |
| Dimefox | Bis (dimethylamino) fluorophosphine oxide |
| Mipafox | Bis (monoisopropylamino) fluorophosphine oxide |
| Systox | Diethylthiophosphoric ester of β-ethyl mercaptoethanol |
| EPN | O-Ethyl o, p-nitrophenyl benzene thiophosphate |

One composition in accordance with the invention successfully employed comprises a mixture of a gasoline fuel with a minor amount of the insecticide malathion. In a series of tests, mixtures containing from about 5% to 20% by volume of a 50% by weight solution of malathion in a gasoline and gasoline-kerosene fuel were employed in two different lawn mowers. The lawn mowers were operated for periods of about one and a half hours (the time necessary to empty a fuel tank) five times over a period of three months without apparent adverse effect upon the lawn mower engines.

The lawn mowers were employed at normal grass cutting intervals during the period July through September 1977 in Sarasota, Fla. The fuel compositions given in Table II below were employed in the various tests. In each case, visual observations of the effect of the exhaust from the engines on insects, including mosquitoes and other flying and crawling insects, were made. Close examination showed that insects were killed by the exhaust fumes, mosquitoes and several varieties of bugs being found dead in the treated area. Live insects were trapped and exposed to the exhaust fumes gathered in a plastic bag and were killed upon such exposure.

Operator observations comparing mowing the lawn with the same lawn mowers powered by gasoline fuels not containing a toxic agent showed that mosquitoes and bugs were not killed. This observation was reinforced by the fact that, when mowing with a conventional gasoline fuel, the operator was bitten by mosquitoes to a considerable extent but when employing a fuel mixture in accordance with the invention during similar hours and under similar conditions there was noticeably less mosquito activity, in fact, virtually none at all on the operator.

The following fuel compositions were employed in these tests in each of the following two lawn mowers, as shown in Table II.

Lawn mower A, a twenty-six inch rotary lawn mower powered by a 3.5 horsepower Briggs & Stratton four-cycle gasoline engine. Lawn mower B is a Bolens riding mower, model number 72,801, powered by a 7 horsepower four-cycle gasoline engine manufactured by Tecumseh-Lauson Engine and Power Products.

Table II

The following mixtures were used in both lawn mower A and lawn mower B.

| Malathion | Gasoline | Kerosene |
|---|---|---|
| % by Weight | | |
| 10 | 15 | 75 |
| 10 | 20 | 70 |
| 5 | — | 95 |
| 10 | — | 90 |
| 20 | — | 80 |

The fuel mixture was prepared in each case by premixing the indicated quantity of malathion with the gasoline or gasoline/kerosene fuel. The mixture was shaken and stirred thoroughly. The malathion was introduced into the mixture in the form of Malathion 50 Insect Spray sold under the trademark ORTHO by the Ortho Division of Chevron Chemical Company, San Francisco, Calif. The label gives the following ingredients:

Malathion—50% by weight;
Aromatic Petroleum Derivative Solvent—33% by weight;
Inert Ingredients—17% by weight.

The lawn mowers were operated in the normal manner without any indications of adverse effect due to the admixture of the insecticide with the fuel. While it is convenient and preferred to thus premix the toxic agent with the fuel, the method of the invention would allow for introducing the fuel and the toxic agent from separate tanks into the combustion chamber of the engine. However, since it is an advantage of the present invention to enable practice of the method without modification to existing equipment such as lawn mowers, cultivators or other agricultural combustion engine powered appliances, it is preferable to premix the toxic agent and fuel and to introduce the mixture of the invention into the conventional fuel tank of the device.

Obviously, any suitable toxic agent required for a specific purpose or purposes which is suitably soluble in the fuel and refractory may be employed. Thus, herbicides would include not only toxic agents designed to kill or control selected plants or weeds, but agents designed to kill or control fungi or other organisms which attack plants which it is desired to save. While a primary objective is to enable the dispensing of an insecticide to control insects, the invention is also applicable to dispensing fumigants or other agents to control other pests such as rodents or the like.

It is necessary that the toxic agent retain its desired qualities of effectiveness despite passing through the engine combustion chamber as mentioned previously and numerous toxic agents are capable of this despite the elevated temperature because of the very short residence time at the elevated temperature. In some cases, an advantage is derived by the intimate admixture of the toxic agent and the oil particles, etc. in the exhaust since this enhances persistence of the toxic agent.

What is claimed is:

1. A method of dispensing a toxic agent over a ground area comprising:
   (a) providing a fuel mixture comprising a mixture of a minor amount of one or more toxic agents effective to control target pests with a major amount of internal combustion engine fuel, the proportion of fuel in said mixture being sufficient to enable operation of an internal combustion engine fueled thereby, said toxic agents being selected from the class consisting of insecticides, fumigants and herbicides which are soluble in said fuel and refractory to fuel combustion conditions of the fueled engine, said toxic agents being present in said mixture in an amount at least sufficient to provide in the exhaust of the fueled engine, an amount of said toxic agent which is effective against such target pests;
   (b) supplying said fuel mixture to the combustion chamber of the internal combustion engine operating a ground vehicle while the vehicle is moving over the ground, the fuel in said mixture being substantially completely combusted; and
   (c) discharging engine exhaust containing said toxic agent in vapor form from the fueled engine into the atmosphere to deposit said toxic agent over the ground area.

2. The method of claim 1 wherein said step of supplying said mixture comprises the step of supplying a mixture of a minor amount of an insecticide with a major amount of gasoline.

3. The method of claim 1 wherein said step of supplying said mixture comprises the step of supplying a mixture of a minor amount of one or more insecticides selected from aldrin, chlordane, dieldrin, DDT, heptachlor, malathion and mirex with a major amount of gasoline.

4. The method of claim 1 wherein said step of supplying said mixture comprises the step of supplying a mixture of a minor amount of malathion with a major amount of gasoline.

5. The method of claim 1 wherein said step of supplying said mixture comprises the step of supplying a mixture of from 2½% to 10% by weight malathion in said fuel.

* * * * *